United States Patent [19]

Simek et al.

[11] Patent Number: 4,508,645

[45] Date of Patent: Apr. 2, 1985

[54] ANALOGS OF NEUROHYPOPHYSIAL HORMONES WITH INHIBITION EFFECTS

[75] Inventors: Petr Simek, Prague; Tomislav Barth, Roztoky; Frantisek Brtnik, Prague; Karel Jost, Prague; Alena Machova, Prague; Linda Servítová, Prague; Jirina Slantinová, Prague, all of Czechoslovakia

[73] Assignee: Ceskoslovenska akademie ved, Prague, Czechoslovakia

[21] Appl. No.: 500,773

[22] Filed: Jun. 3, 1983

[30] Foreign Application Priority Data

Jun. 3, 1982 [CS] Czechoslovakia ............... 4128-82
Aug. 26, 1982 [CS] Czechoslovakia ............... 6206-82

[51] Int. Cl.³ ............... C07C 103/52; A61K 37/00
[52] U.S. Cl. ............................................. 260/112.5 R
[58] Field of Search ............... 260/112.5 R; 424/177

[56] References Cited

PUBLICATIONS

Schröder, et al., The Peptides II, (1966), 320–325, 334, 335, 366–371, 374 & 375.

Primary Examiner—Delbert R. Phillips

[57] ABSTRACT

The invention pertains to analogs of neurohypophysial hormones evidencing inhibition effects of the chemical formula I

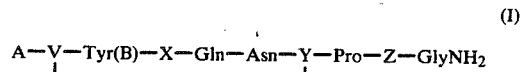

(I)

where A is $CH_3CO$ or H, V is a residue of penicilamine or cysteine, B is $CH_3$ or H, X is a residue of isoleucine or phenylalanine, Y is a residue of penicilamine or cysteine, and Z is a residue of leucine or lysine.

These analogues evidence inhibition effects towards certain biological activities of neurohypophysial hormones.

10 Claims, No Drawings

ANALOGS OF NEUROHYPOPHYSIAL HORMONES WITH INHIBITION EFFECTS

This invention relates to analogs of neurohypophysial hormones with inhibition characteristics. More particularly, the present invention relates to analogs of neurohypophysial hormones which evidence an inhibition effect toward certain biological activities of neurohypophysial hormones. The described inhibitors serve to prove the presence of such hormones in body liquids and also are useful in medical applications, i.e., in connection with a pathological overproduction of endogenous hormones.

Heretofore, two mechanisms have been known for effecting inhibition in the oxytocin molecule. The first of these involves the replacement of the hydroxyl group of tyrosine in the 2 position with a methoxy group described by Berankova et al in Czech. Chem. Commun. 26, 2673 (1961). In this procedure, the inhibition effect may be pronounced by the simultaneous acetylation of the α-amino group of cysteine in the 1 position (Jost et al, Collect, Czech. Chem. Commun. 36, 297 (1971). A second procedure involves the introduction of two methyl groups (Schulz et al, S. Med. Chem. 9, 647 1966), two ethyl groups (Vavrek et al, S. Med. Chem. 15, 124 1972), or a polymethylene chain (Nestor et al, J. Med. Chem. 18, 184 1975) into the beta-position of β-mercaptopropionic acid combined with alkylation of tyrosine (Sawyer et al, Mol Cell. Endocrinol. 22, 117 1981).

It has now been determined that the mutual combination of structural changes such as the alkylation of tyrosine and the introduction of two methyl groups into the beta position of cysteine in position 1 of the peptide chain, with the contingent acetylation of the primary amino group of cysteine, yields compounds with specific inhibition effects toward all action of oxytocin and vasopressin. Furthermore, analogs of vasopressin with a penicilamine residue in the 6 position or in the 1 and 6 positions evidence similar strong inhibition properties.

In accordance with the present invention, the novel analogs of neurohypophysial hormones evidencing inhibition effects are of the formula

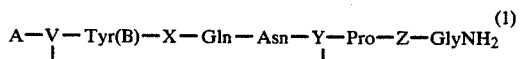

wherein all chiral amino acids are of the L-series and
(a) A is selected from among CH$_3$CO and H,
(b) V is a residue of penicilamine indicated as Pen, or Cys,
(c) B is selected from among CH$_3$ and H,
(d) X is selected from among Ile and Phe,
(e) Y is selected from among Cys and Pen, and P0 (f) Z is selected from among Leu and Lys.

Analogs which are of particular interest are as follows:

| | |
|---|---|
| [1-N-acetylpenicilamine]oxytocin | (Ia) |
| [1-Penicilamine, 2-O-methyltyrosine]oxytocin | (Ib) |
| [1-N-acetylpenicilamine, 2-O-methyltyrosine]oxytocin | (Ic) |
| [1-Penicilamine, 8-lysine]vasopressin | (Id) |
| [1-N-Actylpenicilamine, 8-lysine]vasopressin | (Ie) |
| [1-Penicilamine, 2-O-methyltyrosine, 8-lysine]vasopressin | (If) |
| [1-N-acetylpenicilamine, 2-O-methyltyrosine, 8-lysine]vasopressin | (Ig) |
| [6-Penicilamine, 8-lysine]vasopressin | (Ih) |
| [1-Penicilamine, 6-penicilamine, 8-lysine]vasopressin | (Ii) |

Individual changes pertaining to the above-identified analogs Ia-Ii are surveyed in Table I.

The described analogs of oxytocin and vasopressin of formula (I) may conveniently be prepared by the oxidation of a linear peptide of the following formula

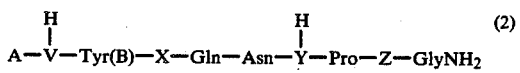

wherein A, B, V, X, Y and Z are as defined above. This oxidation, which may be effected by conventional techniques, yields a disulfide bond.

Certain biological effects of the analogs of oxytocin and vasopressin are set forth in Table I. The inhibition effects of compounds in an in vitro test are expressed as values of pA$_2$, which is the negative logarithm of the molar concentration of inhibitor. This reduces the response of 2X units of an agonistic compound to be equal to the response of 1X units in the absence of inhibitor (Schild, Brit. J. Pharmacol. 2, 189, 1947; Dyckes et al, J. Med. Chem. 17, 160, 1974). In an in vivo test (uterus in vitro), the value of pA$_2$ corresponds with the negative logarithm of an inhibitor constant according to the relationship $$pA_2 = -\log \frac{B}{(A_{50E} - 1)/A_{50}}$$

wherein B is the concentration of inhibitor (M), A$_{50}$ is the concentration of agonistic compound leading to 50% of the maximum effect, and A$_{50B}$ is the concentration of agonistic compound leading to 50% of the maximum effect in the presence of inhibitor B (Eggena et al, J. Gen. Physiol. 52, 465, 1968).

The methods employed in the exemplary embodiments include the following:

Amino acid analyses were conducted with an automatic device, designated Type 6020 of Development Workshops, Czechoslovak Academy of Sciences. Samples of peptides were hydrolyzed in 6M HCl at a reduced pressure of 150 Pa at 105° C. for 20 hours. Oxidations were effected with performic acid. In the thin-layer chromatography process, silica gel plates (Silufol, Kavalier—Czechoslovakia) were run in the following systems:

1. 2-butanol-98% formic acid-water (75:13.5:11.5; S1),
2. 2-butanol-25% aqueous ammonia-water (85:7.5:7.5; S2),
3. 1-butanol-acetic acid-water (4:1:1; S3),
4. 1-butanol-pyridine-acetic acid-water (15:10:3:6; S4), and
5. methanol-chloroform-acetic acid-water (10:15:3:2; S6)

The analytical electrophoresis was carried out on paper (Whatman 3 mm) in a wet chamber at a potential gradient of 20 V/cm for 1 hour in 1M acetic acid (pH 2.4) and in a pyridine-acetate buffer (pH 5.7). The preparative free-flow electrophoresis was carried out in the above-noted device (Prusik et al, Physiol. Chem. 353, 1837, 1972). The high performance liquid chromatography was effected in an apparatus assembled from commercially available parts and columns packed with Separon SI-C18 (Laboratory Instrument Works, Prague).

Several examples of the practice of the present invention are set forth below. These examples are intended to be for purposes of exposition only and it will be appreciated by those skilled in the art that they are not limiting in nature.

EXAMPLE 1

0.56 gram of the amide of O-nitrobenzenesulfenyl-O-tert-butyltyrosyl-isoleucyl-glutaminyl-asparaginyl-S-benzylcysteinylprolyl-leucyl-glycine N-Hydroxysuccinimide ester of o-nitrobenzenesulfenyl-O-tert-butyltyrosine was added to a solution of 1.25 g of the amide of isoleucyl-glutaminyl-asparaginyl-S-benzylcysteinyl-prolyl-leucyl-glycine (Jost et al, Collect. Czech. Chem. Commun. 26, 2496, 1961) in 25 ml of dimethyl-formamide. After two days of stirring, a further portion of the active ester (0.05 g) was added and stirring continued for another 24 hours. Dimethylforamide was then evaporated, the residue triturated with petroleum ether and ether, filtered, and washed with water, 0.1M $H_2SO_4$, water, 0.25M $NaHCO_3$, and water. A product was obtained in a yield of 1.2 g (65%); m.p. 225°–229° C., $[\alpha]_D$ 0° (c 0.2., dimethylformamide); $R_F$ 0.51 (S1), 0.36 (S2), 0.65 (S3), 0.74 (S4). Analysis of amino acids: Tyr 0.94, Ile 0.94, Glu 1.03, Asp 1.06, Cys(Bzl) 0.95, Pro 0.95, Leu 1.08, Gly 1.04. For $C_{57}H_{80}N_{12}O_{13}S_2.H_2O$ (1223) calculated: 55.96% C, 6.76% H, 13.74% N; found: 55.97% C, 6.57% H, 13.70% N.

The amide of benzyloxycarbonyl-S-benzyl-penicilaminyltyrosyl-isoleucyl-glutaminyl-asparaginyl-S-benzylcysteinylprolyl-leucyl-glycine was prepared.

To a solution of 1.1 grams of the above prepared octapeptide in 15 ml of dimethylformamide, there was added 1 ml of 2.05M HCl in ether. Hydrochloride was precipitated with ether after 7 minutes of standing; $E_{2.4}^{Gly}$ 0.59, $D_{5.7}^{His}$ 0.33; $R_F$ 0.25 (S1), 0.17 (S2), 0.24 (S3), 0.64 (S4). Then, the hydrochloride was dissolved in dimethylformamide (10 ml), the pH adjusted with N-ethylpiperidine to 7.5–8.0 (wetted pH-paper), and 0.4 gram of the p-nitrophenyl ester of benzyl-oxycarbonyl-S-benzylpenicilamine in 3 ml of dimethylformamide was added to the solution. After 2 days of stirring, a further portion of the active ester (0.04 g) was added and stirring continued for another 2 days. Dimethylformamide was then evaporated and the residue tirturated with petroleum ether and ether, filtered, and washed with water, 1M HCl, water 0.25M $NaHCO_3$, and water. The resultant compound (0.77 g) was dissolved in 77 ml of trifluoroacetic acid, and allowed to stand at ambient temperature for 1 hour. Then, 77 ml of toluene was added to the reaction mixture, and the solution evaporated to dryness. The residue was triturated with ether, filtered, and dried in a dessiccator over $P_2O_5$ and KOH; 0.7 g (57%) of the product resulted. A part of this compound (0.5 g) was refined by gel filtration in two portions, 0.25 g each. The product was isolated by evaporation of dimethylformamide and trituration of the residue with ether. A product was obtained in a yield of 0.27 g (54%); m.p. 228°–231° C.; $[\alpha]_D$ −42.1° (c 0.2, dimethylformamide); $R_F$ 0.54 (S1), 0.33 (S2), 0.66 (S3), 0.77 (S4). Analysis of amino acids: Pen(Bzl) 0.96, Tyr 0.93, Ile 0.95, Glu 0.99, Asp 1.02, Cys(Bzl) 0.89, Pro 1.04, Leu 1.02, Gly 0.97, For $C_{67}H_{90}N_{12}O_{14}S_2.H_2O$ (1370) calculated 58.75% C, 6.77% H, 12.27% N; found: 58.70% C, 6.53% H, 12.33% N.

The amide of acetyl-S-benzlpenicilaminyl-tyrosyl-isoleucyl-glutaminyl-asparaginyl-S-benzylcysteinyl-prolyl-leucyl-glycine was prepared.

To a solution of 245 mg of the above prepare nonapeptide in 2 ml of acetic acid there was added 2 ml of 35% HBr in acetic acid. Hydrobromide was precipitated with ether after 15 min. of standing at ambient temperature; $E_{2.4}^{Gly}$ 0.51; $R_F$ 0.42 (S1), 0.09 (S2), 0.43 (S3), 0.62 (S4). Hydrobromide was then dissolved in 2.5 ml of dimethylformamide, the solution adjusted to a pH of 7.5–8.0 (wetted pH-paper) with N-ethylpiperdine, and 106 mg of 5-chloro-8-hydroxyquinolinyl ester of acetic acid added. After two days of stirring, a further part of the active ester (20 mg) was added and stirring continued for another 24 hours. Dimethylformamide was then evaporated, the residue triturated with petroleum ether an ether, filtered, and washed with water, 1M HCl, water, 0.25M $NaHCO_3$, and water. A product was obtained in a yield of 185 g (70%) sand further refined by gel filtration yielding 151 mg (82%, overall yield 57%) of a product of m.p. 226°–231° C., $[\alpha]_D$ −39.7° (c 0.1, dimethylformamide); $R_F$ 0.49 (S1), 0.24 (S2), 0.58 (S3), 0.73 (S4). For $C_{61}H_{86}N_{12}O_{13}S_2.0.5H_2O$ (1269) calculated: 57.76% C, 6.91% H, 13.25% N; found: 57.73% C, 6.89% H, 13.57% N.

N$\alpha$-Acetyl[1-penicilamine]oxytocin (Ia)

138 mg of the protected nonapeptide described above was dissolved in 150 ml of boiling liquid ammonia and reduced with sodium until a blue coloration of the reaction mixture was stable for 10 sec. The solution was then decolorized with ammonium chloride, and ammonium removed by freeze-drying. The residue was dissolved in 0.01M HCl (100 ml), diluted with water to a total volume of 300 ml, and the solution adjusted to a pH of 7.0 with 0.01M NaOH. Oxidation was carried out with $3.3 \times 10^{-2}$M $K_3[Fe(CN)_6]$, which was added until a yellow color of the reaction mixture was stable for 1 hour. During oxidation the pH of the reaction mixture was maintained in the region of 6.9–7.0. The reaction mixture was acidified with 1M HCl to a pH of 4.1 and applied on a column packed with a weak-basic anion exchanger in a chloride cycle (50 ml). The column was eluted with 50 ml of water and combined eluates were desalted on a column packed with Separon SI-C18. The column was washed with water and then the product eluted with 90% methanol. The eluate was adicified with acetic acid to a pH of 4.5 and methanol evaporated. A product was obtained by freeze-drying in a yield of 72 mg; 35 mg of it was refined by high-pressure liquid chromatography (methanol-water 4:6) yielding 11 mg of a pure product; $[\alpha]_D$ −47.0° (c 0.18, 3M acetic acid); $R_F$ 0.64 (S4), 0.76 (S6). Analysis of amino acids: Pen($O_3$H)+Cys($O_3$H) (2.00), Tyr 0.97 (0.66), Ile 1.00 (1.00), Glu 0.97 (1.00), Asp 0.97 (1.00), Pro 1.03 (0.77), Leu 1.06 (1.00), Gly 1.00 (1.00). The values in parentheses hold for the sample oxidized with performic acid. For $C_{47}H_{72}N_{12}O_{13}S_2.2CH_3COOH.6H_2O$ (1305) calculated: 46.92% C, 7.10% H, 12.87% N; found: 46.87% C, 6.72% H, 12.81% N.

EXAMPLE 2

The amide of tert-butyloxycarbonyl-O-methyltryrosyl-isoleucyl-glutaminyl-asparaginyl-S-benzylcysteinyl-prolylleucyl-glycine.

2.1 g of the above described heptapeptide was dissolved in 50 ml of dimethylformamide and 1.1 g of 2,4,5-trichlorophenyl ester of tert-butyloxycarbonyl-O-methyltyrosine was added to the solution. After two days of stirring a further portion of the active ester (0.2 g) was added and stirring continued overnight. Dimethylformamide was then evaporated, the residue triturated with petroleum ether and ether, filtered, and washed with water, 5% citric acid, water, 0.25M NaHCO$_3$, and water.

A product was obtained in a yield of 1.9 g (67%); m.p. 225°–228° C., $[\alpha]_D$ −35.2° (c 0.2, dimethylformamide); $R_F$ 0.50 (S1), 0.32 (S2), 0.59 (S3), 0.72 (S4). Analysis of amino acids: Tyr (Me)+Tyr 0.93, Ile 0.96, Glu 0.99, Asp 1.01 Cys(Bzl) 1.03, Pro 1.02, Leu 1.04, Gly 1.00. For $C_{53}H_{79}N_{11}O_{13}S.0.5H_2O$ (1119) calculated: 56.87% C, 7.20% H, 13.76% N; found: 56.62% C, 7.10% H, 13.73% N.

The amide of benzyloxycarbonyl-S-benzyl-penicilaminyl-O-methyltyrosyl-iso-leucyl-glutaminyl-asparaginyl-S-benzylcysteinyl-prolylleucyl-glycine was prepared.

To a solution of 1.5 g of the above prepare octapeptide in 15 ml of acetic acid there was added 15 ml of 35% HBr in acetic acid. Hydrobromide was precipitated with ether after 5 min. at ambient temperature; $E_{2.4}^{Gly}$ 0.57, $E_{5.7}^{His}$ 0.27; $R_F$ 0.23 (S1), 0.20 (S2), 0.34 (S3), 0.59 (S4). Hydrobromide was dissolved in dimethylformamide (15 ml), the solution adjusted to a pH of 7.5–8.0 (wetted pH-paper) with N-ethylpiperdine, and 0.7 g of p-nitrophenyl ester of benzyloxycarbonyl-S-benzylpenicilamine in 4 ml of dimethylformamide was added to this solution. After 4 days of stirring, dimethylformamide was evaporated, the residue triturated with petroleum ether and ether, filtered, and washed with water, 1M HCl, water, 0.25M NaHCO$_3$, and water.

A product was obtained in the amount of 1.0 g (54%) and further purified by gel filtration in four parts, each of 0.25 g.

A product was obtained in a yield of 0.59 g (59%, overall yield 32%); m.p. 233°–239° C., $[\alpha]_D$ −40.2° (c 0.2, dimethylformamide); $R_F$ 0.54 (S1), 0.33 (S2), 0.66 (S3), 0.76 (S4). Analysis of amino acids: Pen(Bzl) 0.87, Tyr (OMe)+Tyr 0.87, Ile 0.94, Glu 0.99, Asp 1.04, (Cys(Bzl) 0.88, Pro 1.04, Leu 1.04, Gly 0.99. For $C_{68}H_{92}N_{12}O_{14}S_2.H_2O$ (1384) calculated: 59.03% C, 6.85% H [1-Penicilamine, 2-O-methyltyrosine]oxytocin (Ib).

238 mg of the above protected nonapeptide was dissolved in 250 ml of boiling liquid ammonia and reduced with sodium until the blue color of the reaction mixture was stable for 30 sec. The solution was decolorized with ammonia chloride, ammonium removed by freeze-drying, and the residue dissolved in 100 ml of 0.01M HCl. The solution was diluted with water to a total volume of 500 ml and the pH adjusted to 7.0 with 0.1M NaOH. Oxidation was then carried out with 3.3×10$^{-2}$M K$_3$[Fe(CN)$_6$], which was gradually added until the yellow color of the reaction mixture was stable for 1 hour. The reaction mixture was maintained at a pH of 6.9–7.0 during oxidation. Next the solution was acidified with 1M HCl to pH of 4.5, and applied on a column packed with a weak-basic anion exchanger in the chloride cycle. The column was then washed with 50 ml of water and the eluate freeze-dried. The resultant compound was purified by a free-flow electrophoresis. A product was obtained in a yield of 23.1 mg; $[\alpha]_D$ 0° (c 0.14, 3M acetic acid); $E_{2.4}^{Gly}$ 0.62, $E_{5.7}^{His}$ 0.23, $R_F$ 0.62 (S4), 0.56 (S6). Analysis of amino acids: Pen(O$_3$H)+Cys(O$_3$H) (2.09), Tyr(Me)+Tyr 0.95 (0.82), Ile 0.96 (0.93), Glu 1.02 (1.02), Asp 1.00 (1.02), Pro 0.98 (0.02), Leu 1.02 (1.00), Gly 1.00 (1.00). The values in parentheses hold for the sample oxidized with performic acid. For $C_{46}H_{72}N_{12}O_{12}S.0.5CH_3COOH.2.5H_2$) (1124) calculated: 50.21% C, 7.08% H, 14.95% N; found: 50.30% C, 6.72% H, 14.94% N.

EXAMPLE 3

The amide of acetyl-S-penincilaminyl-O-methyltyrosyl-isoleucyl-glutaminyl-asparaginyl-S-benzylcysteinyl-propylleucyl-glycine was prepared.

190 mg of the nonapeptide was dissolved in 2 ml of acetic acid and 2 ml of 35% HBr in acetic acid added. Hydrobromide was precipitated with ether after 10 min of standing at ambient temperature; $E_{2.4}^{Gly}$ 0.50; $R_F$ 0.47 (S1), 0.28 (S2), 0.44 (S3), 0.63 (S4). Hydrobromide was then dissolved in 5 ml of dimethylformamide, the solution adjusted to a pH of 7.5–8.0 with N-ethyl-piperdine (wetted pH-paper), and 39 mg of 5-chloro-8-hydroxyquinolinyl ester of acetic acid added to the solution. After two days of stirring a further portion of the active ester was added and stirring continued for another 2 days. Dimethylformamide was evaporated, the residue triturated with petroleum ether and ether, filtered, and washed with water, 1M HCl, water, 0.25M NaHCO$_3$, and water. A product was obtained in a yield of 140 mg (79%) and was further refined by gel filtration to yield 97 mg of a product of m.p. 234°–238° C., $[\alpha]_D$ −47.2° (c 0.1, dimethylformamide); $R_F$ 0.49 (S1), 0.27 (S2), 0.55 (S3), 0.73 (S4). For $C_{62}H_{88}N_{12}O_{13}S_2.2H_2O$ (1310) calculated: 56.86% C, 7.08% H, 12.83% N; found: 56.61% C, 6.84% H, 12.76% N.

Nα-Acetyl[1-peninicilamine, 2-O-methyltyrosine]oxytocin (Ic).

87 mg of the above described protected nonapeptide was dissolved in 100 ml of boiling liquid ammonia and reduced with sodium until a blue color of the reaction mixture was stable for 10 sec. The solution was decolorized with ammonium chloride and ammonia removed by freeze-drying. The residue was dissolved in 100 ml of 0.01M HCl and diluted to a volume of 400 ml. Oxidation was carried out with 3.3×10$^{-2}$M K$_3$[Fe(CN)$_6$], which was gradually added until a yellow color of the reaction mixture was stable for 1 hour. The solution was acidified with 1M HCl to a pH of 4.5 and applied on a column packed with a weak-basic anion exchanger in the chloride cycle (50 ml). The column was eluted with 50 ml of water and the eluate was freeze-dried. The compound was further purified by a counter-current distribution in the system sec-butanol-0.05% aqueous acetic acid (1:1). After 100 transfers of the upper phase and 100 transfers of the lower phase, the compound was isolated from tubes 44–56 and further refined by gel filtration. A product of $[\alpha]_D$ −67.0° (c 0.10, 3M acetic acid); was obtained in a yield of 7.1 mg; $R_F$ 0.64 (S4), 0.83 (S6). Analysis of amino acids: Pen(O$_3$H)+Cys(O$_3$H) (2.05), Tyr(Me)+Tyr 0.98 (0.35), Ile 0.98 (1.00), Glu 1.05 (1.03), Asp 1.00 (1.01), Pro 0.96 (0.95), Leu 1.00 (1.00), Gly 1.00 (1.00). The values in parentheses relate to the sample oxidized with performic acid. For $C_{48}H_{74}N_{12}O_{13}S_2.6H_2O$ (1199) calculated: 48.07% C, 7.23% H, 14.01% N; found: 48.09% C, 7.34% H, 14.23% N.

EXAMPLE 4

The amide of o-nitrobenzenesulfenylasparaginyl-S-benzylcysteinyl-prolyl-$N^\epsilon$-p-toluenesulfonyllysyl-glycine was prepared.

14.0 g of the amide of S-benzylcysteinyl-propyl-N-p-toluenesulfonyllysyl-glycine was dissolved in 70 ml of dimethylformamide and the solution adjusted to a pH of 7.5–8.0 with N-ethylpiperidine (wetted pH-paper). 11.0 g of 2,4,5-Trichlorophenyl ester of o-nitrobenzenesulfenylasparagine was added to the solution and the mixture stirred at ambient temperature.

A further portion of the active ester (1.0 g) was added after 24 hours and stirring continued for another 24 hours. Dimethylformamide was then evaporated and the residue triturated with petroleum ether and ether, filtered and washed with water, 0.1M $H_2SO_4$, water, 0.25M $NaHCO_3$, and water. A product of m.p. 175°–179° C. was obtained in a yield of 15.1 g (76%); $[\alpha]_D - 62.1°$ (c 0.2, dimethylformamide) $R_F$ 0.55 (S1), 0.39 (S2), 0.60 (S3), 0.69 (S4). Analysis of amino acids: Asp 0.97, Cys(Bzl) 0.98, Pro 1.03, Gly 1.01. For $C_{40}H_{51}N_9O_{10}S_3$ (914.1) calculated: 52.56% C, 5.62% H, 13.79% N; found: 52.23% C, 5.54% H, 13.70% N.

The amide of o-nitrobenzenesulfenylglutaminyl-asparaginyl-S-benzyl-cysteinyl-prolyl-$N^\epsilon$-p-toluenesulfonyllsyl-glycine was prepared.

To a solution of 14.0 g of the above prepare compound in 50 ml of dimethylformamide then was added 2.26M HCl in ether. After 7 min of standing, hydrochloride was precipitated with ether and reprecipitated with ether from the solution in dimethylformamide yielding 12.3 g of the compound; $E_{2.4}^{Gly}$ 0.76, $E_{5.7}^{His}$ 0.42, $R_F$ 0.23 (S1), 0.21 (S2), 0.21 (S3), 0.64 (S4). Hydrochloride was dissolved in 50 ml of dimethylformamide, the solution adjusted to a pH of 7.9 g of 2,4,5-trichlorophenyl ester of o-nitrobenzenesulfenylglutamine added. A further portion of the active ester (0.8 g) was added after 24 hours of stirring. After another 24, dimethylformamide was evaporated and the residue triturated with petroleum ether and ether, filtered, and washed with water, 0.1M $H_2SO_4$, water, 0.25M $NaHCO_3$, and water. A product of m.p. 187°–192° C. was obtained in a yield of 10.5 g (65%); $[\alpha]_D - 43.0°$ (c 0.2, dimethylformamide); $R_F$0.38 (S1), 0.24 (S2), 0.49 (S3), 0.69 (S4). Analysis of amino acids; Glu 1.08, Asp 1.07, Cys(Bzl) 0.72, Pro 1.01, Gly 1.06. For $C_{45}H_{59}N_{11}O_{12}S_3 \cdot H_2O$ (1060) calculated: 50.98% C, 5.80% H, 14.53% N; found: 50.79% C, 5.74% H, 14.61% N.

The amide of o-nitrobenzenesulfenylphenylalanyl-glutaminyl-asparaginyl-S-benzylcysteinyl-prolyl-$N^\epsilon$-p-toluenesulfonyllysyl-glycine was prepared.

To a solution of 10 g of the above prepared compound in 50 ml of dimethylformamide there was added 8.9 ml of 2.26M HCl in ether. After 7 min of standing, hydrochloride was precipitated with ether and repeatedly triturated with ether; $E_{2.4}^{Gly}$0.70, $E_{5.7}^{His}$0.40; $R_F$ 0.09 (S1), 0.10 (S2), 0.09 (S3), 0.55 (S4).

Hydrochloride was then dissolved in 40 ml of dimethylformamide, the solution adjusted to a pH of 7.8–8.0 with N-ethylpiperdine (wetted pH-paper), and 4.6 g of 2,4,5-trichlorophenyl ester of o-nitrobenzenesulfenyl-phenylalanine added. After 24 hours of stirring, a further portion of the active ester (1.0 g) was added and stirring continued for another 24 hours. Dimethylformamide was evaporated and the residue triturated with ether and petroleum ether, filtered, and washed with water, 0.1M $H_2SO_4$, water, 0.25M $NaHCO_3$, and water. A product of m.p. 206°–209° C. was obtained in a yield of 8.5 g (74%); $[\alpha]_D - 24.0°$ (c 0.2, dimethylformamide); $R_F$0.53 (S1), 0.29 (S2), 0.58 (S3), 0.72 (S4). Analysis of amino acids: Phe 1.05, Glu 1.05, Asp 1.03, Cys(Bzl) 0.83, Pro 1.03, Gly 1.01. For $C_{54}H_{68}N_{12}O_{13}S_3 \cdot 0.5H_2O$ (1198) calculated: 54.12% C, 5.80% H, 14.02% N; found: 54.02% C, 5.64% H, 14.32% N.

The amide of o-nitrobenzenesulfenyl-O-tert-butyl-tyrosyl-phenylalanyl-glutaminyl-asparaginyl-S-benzyl-cysteinyl-prolyl-N-p-toluenesulfonyllysyl-glycine was prepared.

To a solution of 2.4 g of the above described heptapeptide in 100 ml of dimethylformamide there was added 5.1 ml of 2.05M HCl in ether. After 7 min of standing, hydrochloride was precipitated with ether; $E_{2.4}^{Gly}$ 0.63, $E_{5.7}^{His}$ 0.37; $R_F$ 0.18 (S1), 0.18 (S2), 0.17 (S3), 0.63 (S4). The hydrochloride was dissolved in 50 ml of dimethylformamide, the solution adjusted to a pH of 7.5–8.0 (wetted pH-paper) with N-ethylpiperidine, and 1.1 g of N-hydroxysuccinimide ester of o-nitrobenzenesulfenyl-O-tert-butyltyrosine added. After 24 hours of stirring, a further portion of the active ester (0.2 g) was added and stirring continued overnight. Dimethylformamide was then evaporated, the residue triturated with petroleum ether and ether, filtered, and washed with water, 0.1M $H_2SO_4$, water, 0.25 M $NaHCO_3$, and water. A product of m.p. 193°–197° C. was obtained in a yield of 2.5 g (88%); $[\alpha]_D - 21.1°$ (c 0.,2, dimethylformamide); $R_F$0.58 (S1), 0.34 (S2), 0.63 (S3), 0.77 S4). Analysis of amino acids; Tyr 0.97, Phe 1.02, Glu 1.05, Asp 0.97, Cys(Bzl) 0.85, Pro 1.06, Gly 1.01. For $C_{67}H_{85}N_{13}O_{15}S_3 \cdot H_2O$ (1427) calculated: 56.41% C, 6.18% H, 12.76% N; found: 56.24% C, 6.03% H, 12.94% N.

The amide of benzyloxycarbonyl-S-benzyl-penicilaminyltyrosyl-phenylalanyl-glutaminyl-asparaginyl-S-benzylcysteinylprolyl-$N^\epsilon$-p-toluenesulfonyllysyl-glycine was prepared.

Hydrochloride was prepared from 1.5 g of the octapeptide by the above described procedure (1.1 ml of 2.05M HCl in ether was used). The hydrochloride was dissolved in 10 ml of dimethylformamide, the solution adjusted to a pH of 7.5–8.0 (wetted pH-paper) with N-ethylpiperdine, and 0.5 g of p-nitrophenyl ester of benzyloxycarbonyl-S-benzylpenincilamine in 4 ml of dimethylformamide added. A further portion of the active ester (0.05 g) was added after 2 days of stirring, which was then continued for another two days. Dimethylformamide was then evaporated and the residue triturated with petroleum ether and ether, filtered, and washed with water, 1M HCl, water, 0.25M $NaHCO_3$, and water. 1.29 g of the resultant product was dissolved in 120 ml of trifluroacetic acid, allowed to stand at ambient temperature for 1 hour, 120 ml of toluene added, and the mixture evaporated in vacuum. The residue was triturated with ether and yielded 1.1 g (66%) of the product; 1.0 g of this product was further refined in four portions (0.25 g each) by gel filtration. The product melting at 136°–141° C. was obtained in a yield of 438 mg (58%); $[\alpha]_D - 31.3°$ (c 0.1, dimethylformamide); $R_F$0.56 (S1), 0.30 (S2), 0.68 (S3), 0.71 (S4). Analysis of amino acids: Pen(Bzl) 0.88, Tyr 0.87, Phe 1.05, Glu 1.01, Asp 0.99, Cys(Bzl) 0.88, Pro 0.99, Gly 1.01. For $C_{77}H_{95}N_{13}O_{16}S_2 \cdot H_2O$ (1573) calculated: 58.80% C, 6.22% H, 11.58% N; found: 58.83% C, 6.10% H, 11.76% N.

[1-Penicilamine, 8-lysine]vasopressin (Id).

144 mg of the protected octapeptide was dissolved in 150 ml of boiling liquid ammonia and reduced with sodium until a blue color of reaction mixture remained stable for 20 sec. The reaction mixture was then decolorized with ammonium chloride and ammonia was removed by freeze-drying. The lyophilized residue was dissolved in 50 ml of 0.01 M HCl, the solution diluted with water to 400 ml, and extracted with ether. Residual ether was removed in vacuum and oxidation was performed with $3.3 \times 10^{-2}$M K$_3$[Fe(CN)$_6$], which was gradually added until a yellow color was stable for 1 hour; the reaction mixture was next kept at a pH of 6.9–7.0 by means of 0.1M NaOH. The reaction mixture, after oxidation, was acidified with acetic acid to a pH of 3.5 and the solution chromatographed in a column packed with a carboxylate cation exchanger (30 ml, 100–200 mesh). The column was washed with 0.25% acetic acid and the product eluted with 50% acetic acid and freeze-dried. 71 mg of the resultant were further purified by a free-flow electrophoresis yielding 13.5 mg of a product with $[\alpha]_D - 12.1°$ C. (c 0.14, 3 M acetic acid); $E_{2.4}^{Gly}$ 0.63, $E_{5.7}^{His}$ 0.61; $R_F$ 0.32 (S4), 0.03 (S6). Analysis of amino acids: Pen(O$_3$H)+Cys(O$_3$H) (1.94), Tyr 0.97 (0.58), Phe 1.01 (0.96), Glu 1.05 (1.03), Asp 1.04 (1.03), Pro 0.99 (0.93), Gly 1.03 (1.00). The values in parentheses relate to the sample oxidized with performic acid. For C$_{48}$H$_{69}$N$_{13}$O$_{12}$S$_2$.3.5CH$_3$COOH.6.5H$_2$O (1412) calculated: 46.80% C, 6.85% H, 12.90% N; found: 46.61% C, 6.06% H, 12.82% N.

EXAMPLE 5

The amide of acetyl-S-benzylpenicilaminyl-tyrosyl-phenylalanyl-glutaminyl-asparaginyl-S-benzylcysteinyl-prolyl-N$^\epsilon$-p-toluene-sulfonyllysyl-glycine was prepared.

200 mg of the above described protected nonapeptide were dissolved in 2 ml of acetic acid and 2 ml of 35% HBr in acetic acid were added. Then the solution was allowed to stand at ambient temperature for 10 min, and hydrobromide was precipitated with ether; $E_{2.4}^{Gly}$ 0.53, $R_F$ 0.55 (S1), 0.16 (S2), 0.54 (S3), 0.62 (S4). The hydrobromide was dissolved in dimethylformamide (5 ml), the solution adjusted to a pH of 7.5–8.0 with N-ethylpiperidine (wetted pH-paper), and 56 mg of 5-chloro-8-hydroxyquinolinyl ester of acetic acid were added. A further portion of the active ester was added after 2 days of stirring, which was then continued for another two days. Dimethylformamide was then evaporated, the residue triturated with ether and petroleum ether, filtered, and washed with water, 1M HCl, water, 0.25 M NaHCO$_3$, and water yielding 126 mg (67%) of a product with m.p. 136°–140° C.; $[\alpha]_D - 7.9°$ (c 0.1, dimethylformamide); $R_F$ 0.54 (S1), 0.24 (S2), 0.60 (S3), 0.72 (S4). For C$_{71}$H$_{91}$N$_{13}$O$_{15}$S$_3$.4H$_2$O (1535) calculated: 55.56% C, 6.50% H, 11.86% N; found: 55.38% C, 6.02% H, 11.83% N.

N$\alpha$-Acetyl[1-penicilame, 8-lysine]vasopressin (Ie).

105 mg of a protected nonapeptide was dissolved in 100 ml of boiling liquid ammonia and reduced with sodium until a blue color of the reaction mixture was stable for 10 seconds. The solution was decolorized with ammonium chloride and ammonia removed by freeze-drying. The residue was dissolved in 100 ml of 0.01M HCl, diluted with water to 400 ml, and extracted with ether. Residual ether was removed from the solution in vacuum. Oxidation was performed with $3.3 \times 10^{-2}$M K$_3$[Fe(CN)$_6$], which was gradually added until a yellow color of solution was stable for 1 hour, while a pH of 6.9–7.0 was maintained by means of 0.1M NaOH. The reaction mixture, after oxidation, was acidified with acetic acid to a pH of 3.5 and chromatographed on a column packed with a carboxylic cation exchanger (20 ml, 100–200 mesh). The column was washed with 0.25% acetic acid and then the product was then eluted with 50% acetic acid. the product was obtained by freeze-drying in a yield of 598 mg and further refined by a free-flow electrophoresis yielding 14.8 mg of a product with $[\alpha]_D - 51.0°$ (c 0.14, 3M acetic acid); $E_{2.4}^{Gly}$ 0.51, $E_{5.7}^{His}$ 0.38; $R_F$ 0.40 (S4), 0.26 (S6). analysis of amino acids: Pen(O$_3$H)+Cys(O$_3$H) (1.88), Tyr 0.94 (0.61), Phe 0.96, (1.02), Glu 1.05 (1.00), Asp 1.12 (1.00), Pro 1.21 (1.00), Lys 0.96 (0.98), Gly 1.02 (0.95). The values in parentheses hold for the sample oxidized with performic acid. for C$_{50}$H$_{71}$N$_{13}$)$_{13}$S$_2$.2CH$_3$COOH.4.5H$_2$O (1328) calculated: 48.86% C, 6.68% H, 13.72% N; found: 48.80% C, 5.94% H. 13.76% N.

EXAMPLE 6

The amide of tert-butyloxycarbonyl-O-methylturosyl-phenylalanyl-glutaminyl-asparaginyl-S-benzylcysteinyl-prolyl-N$^\epsilon$-p-toluene-sulfonyllysyl-glycine was prepared.

The hydrochloride was prepared from 2.4 grams of heptapeptide by the procedure described in the preceding examples (5.1 ml of 2.05M HCl in ether was used). The hydrochloride was dissolved in 50 ml of dimethylformamide, the solution adjusted with N-ethylpiperidine to a pH of 7.5–8.0 (wetted pH-paper), and 1 gram of 2,4,5-trichlorophenyl ester of tert-butylcarbonyl-O-methyltyrosine added. A further portion of the active ester (0.2 g) was added after 24 hours of stirring, which was then continued for another 24 hours. Dimethylformamide was then evaporated and the residue triturated with petroleum ether and ether, filtered, and washed with water, 10% citric acid, water, 0.25M NaHCO$_3$, and water. A product with a m.p. of 196°–200° C. was obtained in a yield of 2.2 g (84%); $[\alpha]_D - 21.6°$ (c 0.2, dimethylformamide); $R_F$ 0.55 (S1), 0.25 (S2), 0.46 (S3), 0.66 (S4). Analysis of amino acids: Tyr+Tyr (Me) 0.92, Phe 0.98, Glu 1.00, Asp 1.00, Cys(Bzl) 0.82, Pro 1.05, Gly 1.00. for C$_{63}$H$_{84}$N$_{12}$O$_{15}$S$_2$.2.5H$_2$O (1359) calculated: 55.70% C, 6.60% H, 12.37% N; found: 55.54% C, 6.22% H, 12.43% N.

The amide of benzyloxycarbonyl-S-benzylpenicilaminyl-O-methylk-tyrosyl-phenylalanyl-glutaminyl-asparagingyl-S-benzylsteinyl-prolyl-N-p-toluenesulfonyllysyl-glycine was prepared.

Hydrobromide was prepared from 1.35 grams of the above described octapeptide dissolved in 10 ml of acetic acid by a common procedure (5 ml 35% HBr in acetic acid was used). The hydrobromide was dissolved in 10 ml of dimethylformamide, the solution adjusted with N-ethylpiperidine to a pH of 7.5–8.0 (wetted pH-paper), and 0.51 gram of p-nitrophenyl ester of benzyloxycarbonyl-S-benzyl-penicilamine in 2 ml of dimethylformamide added. A further portion of the active ester (0.25 g) in dimethylformamide (2 ml) was added after 2 days of stirring, which was then continued for another two days. Dimethylformamide was then evaporated, the residue triturated with petroleum ether and ether, filtered, and washed with water, 1M HCl, water, 0.25M NaHCO$_3$, and water yielding 1.2 g (74%) of the product. A part (0.75 g) of this compound was further purified by gel filtration in three portions, 0.25 g each. A product with a m.p. 202°–205° was obtained in a yield of 361 mg (49%); $[\alpha]_D - 34.6°$ (c 0.1, dimethylformamide); $R_F$ 0.60 (S1), 0.31 (S2), 0.68 (S3), 0.76 (S4). Analysis of amino acids: Pen (Bzl) 1.04, Tyr+Tyr(Me) 0.94, Phe 1.03, Glu 1.00, Asp 0.99, Cys(Bzl) 0.92, Pro 1.00, Gly 1.00. for $C_{78}H_{97}N_{13}O_{16}S_3 \cdot 1.5H_2O$ (1596) calculated: 58.70% C, 6.31% H, 11.41% N; found: 58.65% C, 6.25% H, 11.57% N.

[1-Penicilamine, 2-O-methyltyrosine, 8-lysine]-vasopressin (If).

145 mg of the above-described nonapeptide was dissolved in 150 ml of boiling liquid ammonia and reduced with sodium until a blue color of the solution was stable for 10 seconds. The solution was decolorized with ammonium chloride and ammonia removed by freeze-drying. The residue was then dissolved in 100 ml of 0.01M HCl, diluted with water to 450 ml, and the solution extracted with ether. Residual ether was removed in vacuum. Oxidation was carried out with $3.3 \times 10^{-3}$M $K_3[Fe(CN)_6]$, which was gradually added until a yellow color of the reaction mixture was stable for 1 hour. During oxidation, the reaction mixture was kept at a pH of 6.9–7.0 by means of 0.1M NaOH. The solution, after oxidation, was acidified with acetic acid to a pH of 4.0 and chromtographed on a column packed with a carboxylate cation exchanger (20 ml, 100–200 mesh). the column was washed with 0.25% acetic acid and the product eluted with 50% acetic acid and freeze-dried yielding 86 mg of a dry substance, which was refined by a free-flow electrophoresis. The product of $[\alpha]_D$ 0° (c 0.15, 3M acetic acid) was obtained in a yield of 10.3 mg; $E_{2.4}{}^{Gly}$ 0.63, $E_{5.7}{}^{His}$ 0.60; $R_F$ 0.34 (S4), 0.05 (S6).

Analysis of amino acids: Pen(O$_3$H)+Cys(O$_3$H) (1.94), Tyr+Tyr (Me) 0.94 (0.82), Phe 1.06 (1.04), Glu 0.96 (1.00), Asp 1.06 (1.00), Pro 1.00 (0.99), Lys 0.97 (1.04), Gly 1.00 (0.99). The values in parentheses relate to the sample oxidized with performic acid. For $C_{49}H_{71}N_{13}O_{12}S_2 \cdot 3CH_3COOH \cdot 6H_2O$ (1369) calculated: 48.27% C, 6.85% H, 13.30% N; found: 48.30% C, 6.27% H, 13.42% N.

EXAMPLE 7

The amide of acetyl-S-benzylpenicilaminyl-O-methyltyrosyl-phenyl-alanyl-glutaminyl-asparaginyl-S-benzylcysteinyl-prolyl-N$^\epsilon$-p-toluenesulfonyllysyl-glycine was prepared. 200 mg of the above-described protected nonapeptide was dissolved in 2 millilieters of acetic acid and 2 ml of 35% HBr in acetic acid was added. Hydrobromide was precipitated with ether after 10 minutes of standing at ambient temperature; $E_{2.4}{}^{Gly}$0.49; $R_F$ 0.07 (S2), 0.63 (S4). The hydrobromide was dissolved in 2 millilieters of dimethylformamide, the solution adjusted to a pH of 7.5–8.0 with N-ethylpiperidine (wetted pH-paper), and 43 mg of 5-chloro-8-hydroxyquinolinyl ester of acetic acid added. A further portion of the active ester (15 mg) was added after 2 days of stirring, which was continued for another two days. Dimethylformamide was then evaporated and the residue triturated with petroleum ether and ether, filtered, and washed with water, 1M HCl, water, 0.25M NaHCO$_3$, and water yielding 142 mg (74%) of a product, which was further purified by gel filtration. The product with a m.p. of 190°–195° C. was obtained in a yield of 109 mg; $[\alpha]_D - 31.2°$ (c 0.1, dimethylformamide); $R_F$ 0.56 (S1), 0.26 (S2), 0.59 (S3), 0.74 (S4). For $C_{72}H_{93}N_{13}O_{15}S_3 \cdot 2.5H_2O$ (1522) calculated: 56.83% C, 6.49% H, 11.96% N; found: 56.50% C, 6.30% H, 11.99% N.

N$\alpha$-Acetyl[1-penicilamine, 2-O-methyltyrosine, 8-lysine] vasopressin.

92 mg of the above-described protected nonapeptide was dissolved in 150 millilieters of boiling liquid ammonia and reduced with sodium until a blue color of the reaction mixture remained for 10 seconds. The solution was decolorized with ammonium chloride and freeze-dried. The dry substance was then dissolved in 100 millileters of 0.01M HCl, diluted with water to 450 ml, and extracted with ether. Residual ether was removed from the solution in vacuum. Oxidation was performed with $3.3 \times 10^{-2}$M $K_3[Fe(CN)_6]$, which was gradually added until a yellow color of the reaction mixture was stable for 1 hour. The reaction mixture was maintained during oxidation at a pH of 6.9–7.0 by means of 0.1M NaOH. The solution, after oxidation, was acidified with acetic acid to a pH of 4.0 and chromatographed on a column packed with a carboxylate cation exchanger (25 ml, 100–200 mesh). The column was washed with 0.25% acetic acid, the product eluted with 50% acetic acid, and the solution freeze-dried yielding 60 mg of a dry substance. This was purified by a free-flow electrophoresis and yielded 2.4 mg of a product with $[\alpha]_D - 32.8°$ (c 0.13, 3M acetic acid); $E_{2.4}{}^{Gly}$ 0.51, $E_{5.7}{}^{His}$ 0.35; $R_F$ 0.43 (S4), 0.39 (S6). Analysis of amino acids: Pen(O$_3$H)+Cys(O$_3$H) (1.96), Tyr+Tyr (Me) 0.96 (0.69), Phe 1.04 (0.49), Glu 1.01 (1.00), Asp 1.03 (1.00), Pro 1.03 (0.97), Lys 0.95 (0.98), Gly 1.03 (1.01). For $C_{51}H_{73}N_{13}O_{13}S_2 \cdot 6CH_3COOH \cdot 7H_2O$ (1628) calculated: 45.51% C, 6.88% H, 11.19% N; found: 46.40% C, 6.43% H, 11.08% N.

EXAMPLE 8

[6-Penicilamine, 8-lysine]vasopression (Ih)

90 mg of the protected nonapeptide, amide of benzyloxycarbonyl-S-benzylcysteinyl-tyrosyl-phenylalanyl-glutaminyl-asparaginyl-S-benzylpenicilaminyl-prolyl-N-p-toluenesulfonyllysyl-glycine, prepared by a sequential building of the peptide chain in solution, was reduced with sodium in 100 ml of liquid ammonia until a blue color of the reaction mixture was stable for 20 sec. The solution was decolorized with ammonium chloride and ammonia removed by freeze-drying. The residue was dissolved in 100 ml of 0.01M HCl, diluted with 50 ml of water, and extracted with ether. Then, the solution was diluted to 300 ml, adjusted to a pH of 7.0, and oxidation performed by gradual addition of $3.3 \times 10^{-2}$M $K_3[Fe(CN)_6]$ until a yellow color of the reaction mixture was stable for 1 hour. During oxidation, the pH value was maintained at 6.9–7.0. The reaction mixture, after oxidation, was acidified with acetic acid to a pH of 4.5 and applied on a column of a carboxylate cation exchanger. The column was washed with 0.25% acetic acid and the product eluted with 50% acetic acid, freeze-dried, and refined by a free-flow electrophoresis. The freeze-dried product of $[\alpha]_D + 13.6°$ (c 0.13, 3M acetic acid) was obtained in a yield of 10.2 mg; $E_{2.4}{}^{His}$ 0.66, $E_{5.7}{}^{His}$ 0.61; $R_F$ 0.33 (S4), 0.03 (S6). Analysis of amino acids: Cys(O$_3$H)+Pen-(O$_3$H) (1.94), Tyr 0.92 (0.56), Phe 1.00 (0.96), Glu 0.92 (0.91), Asp 1.00 (1.01), Pro 1.00 (1.03), Lys 1.07 (0.98), Gly 0.96 (1.07). The values in parentheses relate to the sample oxidized with performic acid. For $C_{48}H_{69}N_{13}O_{12}S_2 \cdot 5CH_3COOH \cdot 8H_2O$ (1529) calculated: 41.81% C, 6.35% H, 10.93% N; found (corrected for 9% ash): 41.50% C, 6.44% H, 10.92% N.

EXAMPLE 9

[Disulfide 1-penicilamine, 6-penicilamine, 8-lysine]vasopressin (Ii)

20 mg of the protected nonapeptide, amide of benzyloxycarbonyl-S-benzylpenicilaminyl-tyrosyl-phenylalanyl-glutaminyl-asparaginyl-S-benzyl-penicilaminyl-prolyl-N-p-tolurenesulfonyllysyl-glycine, prepared by a sequential building of the peptide chain in solution, was reduced with sodium in liquid ammonia, oxidized with potassium ferricyanide, and purified in the maner described in Example 1. A product was obtained in a yield of 10.5 mg; $[\alpha]_D -11.0°$ (c 0.13, 3M acetic acid); $E_{2.4}^{His}0.61$, $E_{5.7}^{His}0.60$, $R_F$ 0.36 (S4), 0.04 (S6). Analysis of amino acids (the values in parentheses relate to the sample oxidized with performic acid): Pen(O$_3$H) (1.80), Tyr 0.86 (0.82), Phe 1.00 (1.06), Glu 0.92 (0.98), Asp 1.00 (0.91), Pro 1.00 (1.13), Lys 1.00 (0.98), Gly 1.00 (0.99). For $C_{50}H_{73}N_{13}O_{12}S_2.3.5CH_3COOH5H_2O(1443)$ calculated: 48.57% C, 6.92% H, 12.89% N; found 48.54% C, 6.80% H, 12.86% N.

We claim:

1. Analog of neurohypophysial hormones evidencing inhibition characteristics of the formula:

$$A-V-Tyr(B)-X-Gln-Asn-Y-Pro-Z-GlyNH_2$$

(with a disulfide bridge between V and Y)

wherein (a) A is selected from the group consisting of CH$_3$CO and H, (b) V and Y are residues both selected from the group consisting of penicillamine and cysteine, at least one of which is penicillamine, (c) B is selected from the groups consisting of CH$_3$ and H, (d) X is a residue selected from the group consisting of isoleucine and phenylalanine, and (e) Z is a residue selected from the group consisting of leucine and lysine.

2. [1-N-acetylpenicilamine]oxytocin.

3. [1-penicilamine, 2-O-methyltyrosine]oxytocin.

4. [1-N-acetylpenincilamine, 2-O-methyltyrosine]oxytocin.

5. [1-penicilamine, 8-lysine]vasopressin.

6. [1-N-acetylpenicilamine, 8-lysine]vasopressin.

7. [1-penicilamine, 2-O-methyltyrosine, 8-lysine]vasopressin.

8. [1-N-acetylpenicilamine, 2-O-methyltyrosine, 8-lysine]vasopressin.

9. [6-penicilamine, 8-lysine]vasopressin.

10. [(1-penicilamine, 6-penicilamine, 8-lysine]vasopressin.

TABLE I

A survey of structure modifications and some biological values of analogues Ia–Ii

| | | | | | | | Inhibition activity pA$_2$ in the determination of efficiency | | | |
|---|---|---|---|---|---|---|---|---|---|---|
| | | | | | | | uterotonic | | | |
| Analogue | A | V | B | X | Y | Z | in vitro | in situ | pressor | galactogogic |
| Ia | CH$_3$CO | Pen | H | Ile | Cys | Leu | 4,4 | —$^a$ | ineffective | 0,04 |
| Ib | H | Pen | CH$_3$ | Ile | Cys | Leu | 8,0 | 6,9 | 7,2 | 6,8 |
| Ic | CH$_3$CO | Pen | CH$_3$ | Ile | Cys | Leu | 5,4 | —$^a$ | 6,4 | 0,45$^b$ |
| Id | H | Pen | H | Phe | Cys | Lys | 6,6 | 6,3 | 6,9 | —$^a$ |
| Ie | CH$_3$CO | Pen | H | Phe | Cys | Lys | 5,5 | 6,3 | ineffective | ineffective |
| If | H | Pen | CH$_3$ | Phe | Cys | Lys | 8,1 | 6,9 | 7,4 | 6,8 |
| Ig | CH$_3$CO | Pen | CH$_3$ | Phe | Cys | Lys | —$^a$ | —$^a$ | 6,7 | ineffective |
| Ih | H | Cys | H | Phe | Pen | Lys | 6,00 | 6,16 | 6,73 | —$^a$ |
| Ii | H | Pen | H | Phe | Pen | Lys | 6,80 | 6,80 | 7,18 | —$^a$ |

$^a$not determined
$^b$agonistic activity in I.U./mg